US009295741B2

(12) United States Patent
Yerby

(10) Patent No.: US 9,295,741 B2
(45) Date of Patent: Mar. 29, 2016

(54) APPARATUS AND METHOD FOR SANITIZING ARTICLES UTILIZING A PLURALITY OF REFLECTOR UNITS TO EVENLY DISTRIBUTE UV RADIATION

(76) Inventor: Earl Yerby, Apex, NC (US)

( * ) Notice: Subject to any disclaimer, the term of this patent is extended or adjusted under 35 U.S.C. 154(b) by 0 days.

(21) Appl. No.: 13/431,632

(22) Filed: Mar. 27, 2012

(65) Prior Publication Data

US 2013/0256560 A1 Oct. 3, 2013

(51) Int. Cl.
*A61L 2/10* (2006.01)
*A61L 2/24* (2006.01)
*A61L 2/26* (2006.01)

(52) U.S. Cl.
CPC ... *A61L 2/10* (2013.01); *A61L 2/24* (2013.01); *A61L 2/26* (2013.01); *A61L 2202/122* (2013.01)

(58) Field of Classification Search
CPC .................................. A61L 2/10; E01F 9/015
USPC .................................. 250/455.11; 359/207.8
See application file for complete search history.

(56) References Cited

U.S. PATENT DOCUMENTS

| 4,128,226 | A |   | 12/1978 | Ross et al. |          |
|-----------|---|---|---------|-------------|----------|
| 4,321,232 | A |   | 3/1982  | Bithell     |          |
| 4,505,545 | A |   | 3/1985  | Salia-Munoz |          |
| 4,623,796 | A | * | 11/1986 | Kratz       | 250/504 R|
| 4,683,886 | A | * | 8/1987  | Kramer et al. | 607/91 |
| 4,835,749 | A | * | 5/1989  | Welton      | 368/10   |
| 4,917,586 | A |   | 4/1990  | Jacob       |          |
| 4,918,319 | A | * | 4/1990  | Kruithof    | 250/504 R|
| 4,959,551 | A | * | 9/1990  | Schlitt     | 250/504 R|
| 5,163,751 | A |   | 11/1992 | Bottiglieri |          |
| 5,225,160 | A |   | 7/1993  | Sanford et al. |       |
| 5,277,516 | A | * | 1/1994  | Strieter    | 404/14   |
| 5,342,582 | A |   | 8/1994  | Horn et al. |          |
| 5,395,591 | A | * | 3/1995  | Zimlich et al. | 422/107 |
| 5,546,678 | A | * | 8/1996  | Dhaemers    | 34/275   |

(Continued)

FOREIGN PATENT DOCUMENTS

CN   2155875 Y   2/1994
EP   1346735 A1   9/2003

(Continued)

OTHER PUBLICATIONS

Examiner calculation of estimate output of Doty's apparatus.*

(Continued)

*Primary Examiner* — Nicole Ippolito
*Assistant Examiner* — Sean Luck
(74) *Attorney, Agent, or Firm* — Michael G. Johnston; Moore & Van Allen PLLC

(57) ABSTRACT

An apparatus is provided for sanitizing an article, the apparatus comprising a housing defining an enclosed internal chamber and having an opening at a door side into the chamber. A door is configured to selectively close the door side of the housing for substantially sealing the chamber. A UV light source is disposed internally of the housing for irradiating the chamber, and an electronic circuit is electrically connected to the UV light source and adapted to power the UV light source for a predetermined period of time. A reflector unit is disposed on one of the walls, the reflector unit including a reflective section projecting outwardly at an angle with respect to the wall. With the article placed in the chamber and the door closed and the electronic circuit activated, the UV lamp is illuminated for the predetermined period of time for sanitizing the article.

15 Claims, 10 Drawing Sheets

(56) References Cited

U.S. PATENT DOCUMENTS

| | | | |
|---|---|---|---|
| 5,597,597 A | 1/1997 | Newman | |
| 5,683,437 A * | 11/1997 | Doty | 607/91 |
| 5,730,934 A | 3/1998 | Holbert | |
| 5,786,598 A | 7/1998 | Clark et al. | |
| 5,791,605 A * | 8/1998 | Howie, II | 246/474 |
| 5,836,669 A | 11/1998 | Hed | |
| 5,843,374 A | 12/1998 | Sizer et al. | |
| 5,879,620 A | 3/1999 | Cohen | |
| 5,993,739 A | 11/1999 | Lyon | |
| 6,083,387 A * | 7/2000 | LeBlanc et al. | 210/199 |
| 6,168,276 B1 * | 1/2001 | Weid | 359/547 |
| 6,461,376 B1 * | 10/2002 | Beshore | 607/91 |
| 6,465,799 B1 * | 10/2002 | Kimble et al. | 250/504 R |
| 6,494,901 B1 * | 12/2002 | Doty | 607/91 |
| 6,605,260 B1 | 8/2003 | Busted | |
| 6,749,806 B2 | 6/2004 | Koji et al. | |
| 6,802,854 B1 * | 10/2004 | McFarland | 607/91 |
| 6,814,932 B2 | 11/2004 | Hlebovy et al. | |
| 6,897,460 B2 | 5/2005 | Kobayashi et al. | |
| 6,923,367 B1 | 8/2005 | Grossman et al. | |
| 7,038,219 B2 | 5/2006 | Clark et al. | |
| 7,160,566 B2 | 1/2007 | Fink et al. | |
| 7,511,283 B2 | 3/2009 | Chor | |
| 7,560,706 B1 | 7/2009 | Castelluccio | |
| 7,791,044 B1 | 9/2010 | Taylor et al. | |
| 7,935,940 B1 * | 5/2011 | Smargiassi | 250/492.1 |
| 2002/0011576 A1 * | 1/2002 | Cho et al. | 250/559.37 |
| 2003/0060853 A1 * | 3/2003 | Unvert et al. | 607/20 |
| 2003/0088297 A1 * | 5/2003 | Stoppler | 607/94 |
| 2003/0150475 A1 * | 8/2003 | Abrams et al. | 134/1 |
| 2003/0155536 A1 * | 8/2003 | Laudano et al. | 250/504 R |
| 2003/0187487 A1 * | 10/2003 | Griffith et al. | 607/94 |
| 2003/0193717 A1 * | 10/2003 | Gubela, Sr. | 359/529 |
| 2004/0084630 A1 * | 5/2004 | Waluszko | 250/455.11 |
| 2004/0088028 A1 * | 5/2004 | Cameron et al. | 607/94 |
| 2004/0217681 A1 * | 11/2004 | Park et al. | 313/110 |
| 2005/0072449 A1 * | 4/2005 | Alpert et al. | 134/25.1 |
| 2005/0230639 A1 | 10/2005 | Ancona et al. | |
| 2005/0240248 A1 * | 10/2005 | Venuto | 607/91 |
| 2005/0269521 A1 * | 12/2005 | Zagrobelny | 250/435 |
| 2005/0274906 A1 | 12/2005 | Riddell | |
| 2006/0162644 A1 * | 7/2006 | Choi | 116/200 |
| 2008/0067425 A1 * | 3/2008 | Kaszuba et al. | 250/492.2 |
| 2008/0125834 A1 * | 5/2008 | Hendrix et al. | 607/88 |
| 2008/0186498 A1 * | 8/2008 | Gubela | 356/445 |
| 2008/0211989 A1 * | 9/2008 | Park | 349/64 |
| 2009/0005839 A1 * | 1/2009 | Griffith et al. | 607/91 |
| 2009/0065716 A1 | 3/2009 | Ullman | |
| 2009/0148358 A1 | 6/2009 | Wind | |
| 2009/0257910 A1 * | 10/2009 | Segal | 422/22 |
| 2010/0044582 A1 | 2/2010 | Cooper et al. | |
| 2010/0148090 A1 | 6/2010 | Chang | |
| 2010/0162951 A1 * | 7/2010 | Pinotti | 118/642 |

FOREIGN PATENT DOCUMENTS

| | | |
|---|---|---|
| EP | 1602878 B1 | 3/2012 |
| KR | 20030086653 | 11/2003 |
| WO | 9517634 | 6/1995 |
| WO | 0160419 A1 | 8/2001 |
| WO | 2005072782 A1 | 8/2005 |
| WO | 2011041491 A1 | 4/2011 |
| WO | 2011055140 A1 | 5/2011 |

OTHER PUBLICATIONS

Yerby, Earl, Australian Application No. 2013239823, Patent Examination Report No. 1, Jan. 12, 2015.

Yerby, Earl, International Application No. PCT/US2013/033984, International Search Report and Written Opinion, Jun. 27, 2013.

* cited by examiner

APPARATUS AND METHOD FOR SANITIZING ARTICLES UTILIZING A PLURALITY OF REFLECTOR UNITS TO EVENLY DISTRIBUTE UV RADIATION

RELATED APPLICATIONS

This application is related to co-pending U.S. patent application Ser. No. 13/431,587, which is a continuation of U.S. application Ser. No. 12/512,766, filed on Jul. 30, 2009, now U.S. Pat. No. 8,143,596, which claims the benefit of U.S. Provisional Patent Application No. 61/268,365, filed on Jun. 11, 2009, all of which applications and patent are incorporated herein by reference in their entirety.

BACKGROUND

An apparatus and method for sanitizing articles is described and, more particularly, an apparatus and method using ultraviolet light for sanitizing articles between uses, such as medical instruments, tools and objects, patient-care items, and the like.

Ultraviolet (UV) light of a particular range of wavelengths, intensities, and durations can kill or inhibit growth of microorganisms. Specifically, ultraviolet radiation in the range of 200 nanometer (nm) to 300 nm is effective against airborne and surface bacteria, viruses, yeasts, and molds. For most microorganisms, the peak inactivation wavelength is at or about 260 nm. Mercury lamps produce UV light very efficiently at 254 nm and, therefore, this wavelength has become the standard UV germicidal light wavelength.

UV light is used in healthcare facilities to disinfect surgical theaters and operating rooms. UV light is also used extensively in air and water purification applications in the food and beverage industry and in sewage treatment. UV light can also be used to disinfect patient-contact items like stethoscopes, thermometers, blood pressure cuffs, and oximeters, as well as doctor and staff-carried items such as cell phones, eMARs scanners, penlights, scissors, PDAs/tablets/laptops, and other easily contaminated, and difficult-to-disinfect items. UV light can also disinfect hand-held and portable electronic devices and other personal articles, including mobile (cellular) telephones, portable music and video players (e.g., MP3 and MP4 players), cameras, portable global positioning devices, and the like.

In conventional UV sanitization devices, the UV radiation sources are stationary or portable and can range in size from very large devices to small hand-held wands. However, a problem associated with UV sanitization is most articles or implements requiring sanitization will have interior spaces and non-planar surfaces. Some will have multiple invaginations which can harbor microbes, such as reusable grocery bags, sporting equipment including helmets and shoes, and the like. Typically, UV sanitization devices are inadequate to irradiate the non-planar surfaces of articles at varying distances from the UV radiation sources. As a result, some surfaces of the articles are not reached by UV irradiation.

For the foregoing reasons, there is a need for a new device for sanitizing articles, particularly articles having an interior space and non-planar surfaces that are difficult to reach with conventional UV irradiation.

SUMMARY

An apparatus is provided for sanitizing an article, the apparatus comprising a housing including a plurality of walls defining an enclosed internal chamber and having an opening at a door side into the chamber. A door is configured to selectively close the door side of the housing for substantially sealing the chamber. A UV light source is disposed internally of the housing for irradiating the chamber, and an electronic circuit is electrically connected to the UV light source and adapted to power the UV light source for a predetermined period of time. A reflector unit is disposed on at least one of the walls, the reflector unit including a reflective section projecting outwardly at an angle with respect to the at least one of the walls. With the article placed in the chamber and the door closed and the electronic circuit activated, the UV lamp is illuminated for the predetermined period of time for sanitizing the article.

BRIEF DESCRIPTION OF THE DRAWINGS

For a more complete understanding of the present invention, reference should now be had to the embodiments shown in the accompanying drawings and described below. In the drawings.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGS. Indeed, the components may be oriented in any direction and the terminology, therefore, should be understood as encompassing such variations unless specified otherwise.

As used herein, the term "article" is deemed to mean any portable, potentially contaminated object or item of porous or non-porous material suspected to be a fomite or vector of pathogens and disease transmission.

As used herein, the terms "bulb" or "lamp" is deemed to mean any source of UV light.

As used herein the terms "disinfect" and "sanitize" is deemed to mean the expectation that bacterial count will be substantially reduced on objects and items irradiated with UV light.

As used herein, the term "reflector unit" means a collection of reflective structures that together reflect at least 60% of light having a frequency between 100 nm to 290 nm.

Figure 1:
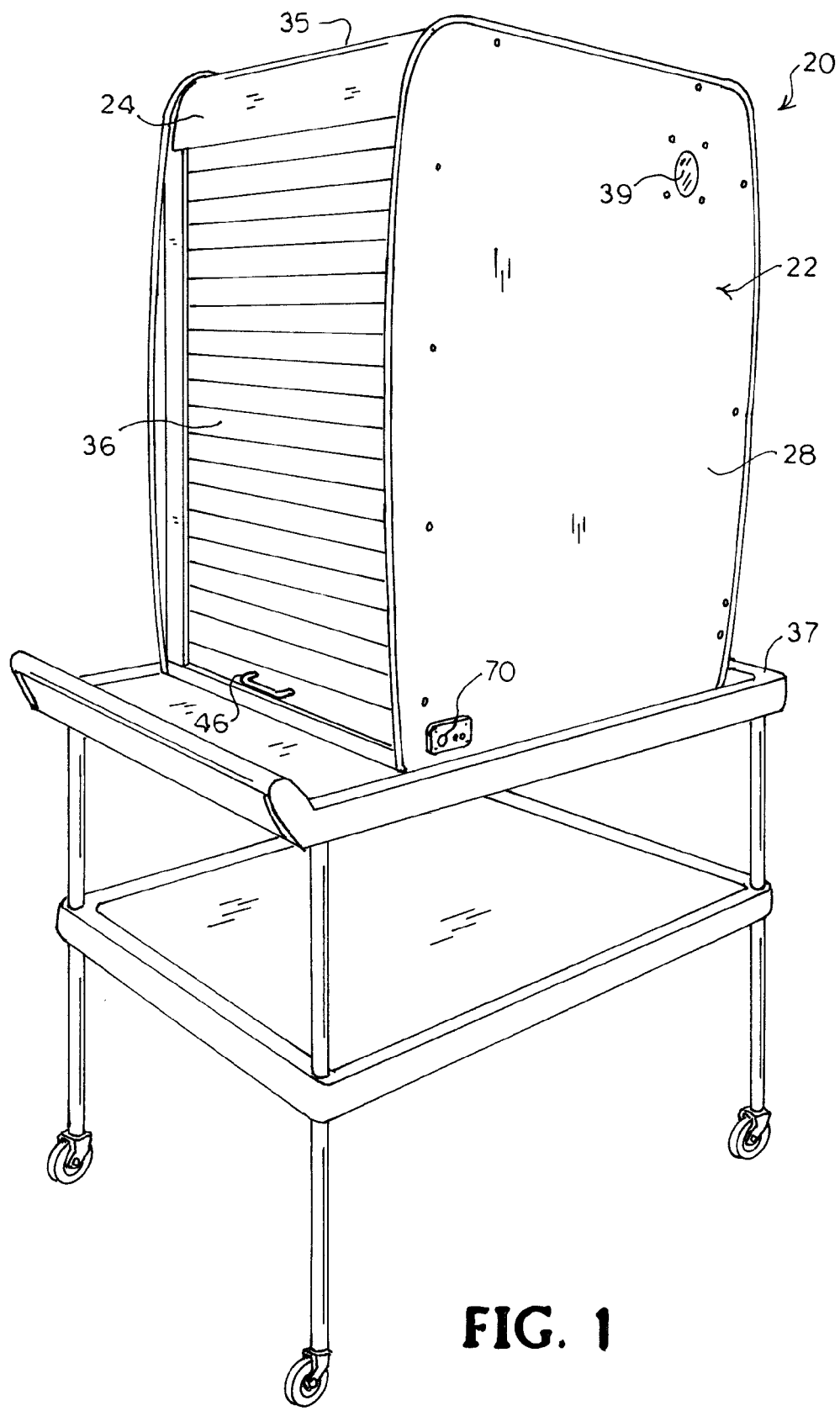
FIG. 1 is a front perspective view of an embodiment of a device for sanitizing articles with a door in a closed position.

A device for sanitizing an article is shown in FIG. 1 and generally designated at 20. The sanitizing device 20 comprises a housing 22 constructed of a material that is impervious to UV radiation. In one embodiment, the housing 22 is formed from polished, reflective aluminum sheeting. The housing 22 is substantially cube-like in shape, including a partial front wall 24 defining an opening 26, side walls 28, and an inner rear wall 30 and an outer rear wall 31 (not visible in FIG. 1). The walls 24, 28, 30, 31 of the housing 22 are joined adjacent their edges by a ceiling 32, a roof 35 spaced from the ceiling and a floor 34. The opening 26 in the front wall 24 is sealed by a sliding tambour door 36, which provides access to inside the housing 22. Optionally, the housing 22 can include a UV-resistant viewing window 39 that allows a user to view the inside of the sanitizing device 20 during operation while avoiding exposure to UV radiation. The housing 22 is sized and shaped to receive an article to be sanitized. The dimensions of the housing 22 may be determined by the field of use. In the embodiment shown in the FIGS., the sanitizing device 20 may be placed on a cart 37 for mobility of the device. Alternatively, the sanitizing device 20 can be mounted to a wall or placed on a table or on the ground. It is understood that the size of the housing 22 or the opening 26 can vary depending on the article to be disinfected. All commercially viable sizes are contemplated.

Figure 2:
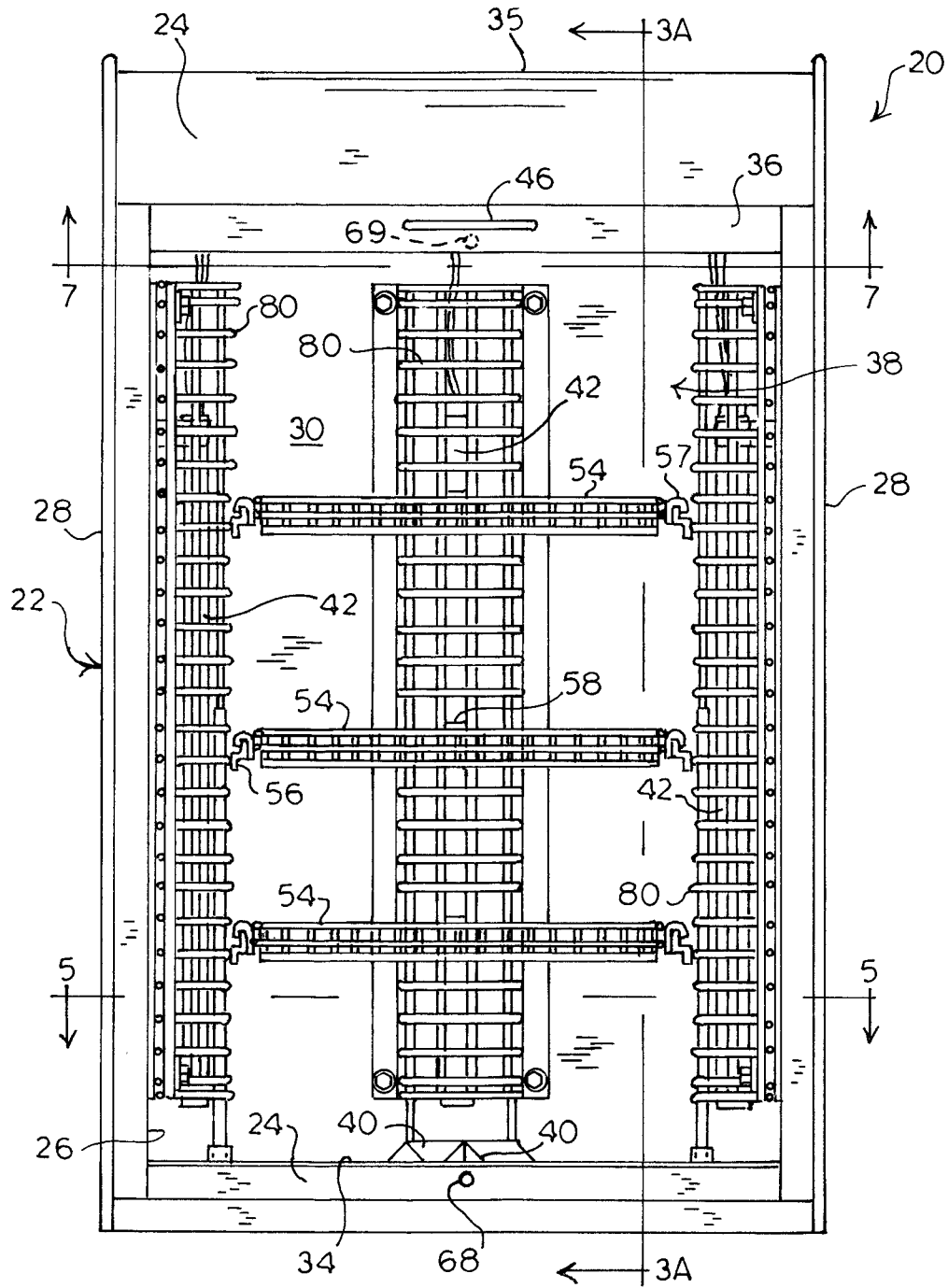
FIG. 2 is a front elevation view of the sanitizing device shown in FIG. 1 with the door in an open position.

Referring to FIG. 2, the housing 22 defines an open interior chamber 38 formed by the inner surfaces of the front and side walls 24, 28, the inner surface of the inner rear wall 30, and inner surfaces of the ceiling 32 and the floor 34. The opening 26 in the front wall 24 allows the user to access the chamber 38 for inserting and removing articles to be sanitized. The chamber 38 is configured to accommodate at least one source of UV radiation with a wavelength and intensity suitable for sanitization of the articles. The sanitizing device 20 may further comprise one or more means for supporting articles to be sanitized. In addition, one or more reflector units 40 project upwardly from the floor 34 for reflecting UV light from the UV lamps 42 upwardly toward the articles disposed within the chamber 38. As described in more detail below, the reflector units 40 provide a more thorough and uniform distribution of UV light to all surfaces within the chamber 38, and in particular, the underside of the article supporting means and the articles.

Figure 3A:
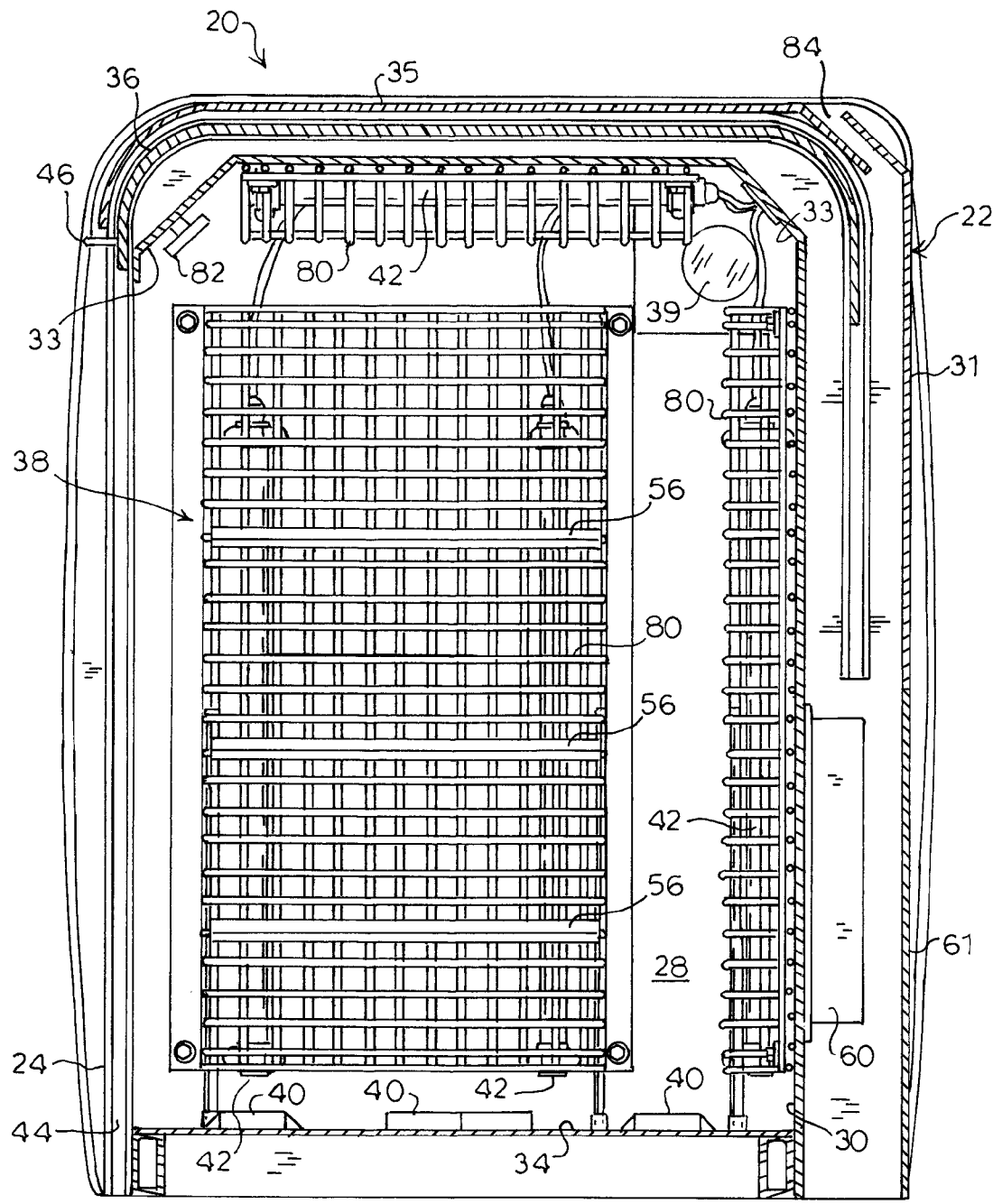
FIG. 3A is a longitudinal cross-section view of the sanitizing device shown in FIG. 1 taken along line 3A-3A of FIG. 2.
Figure 3B:
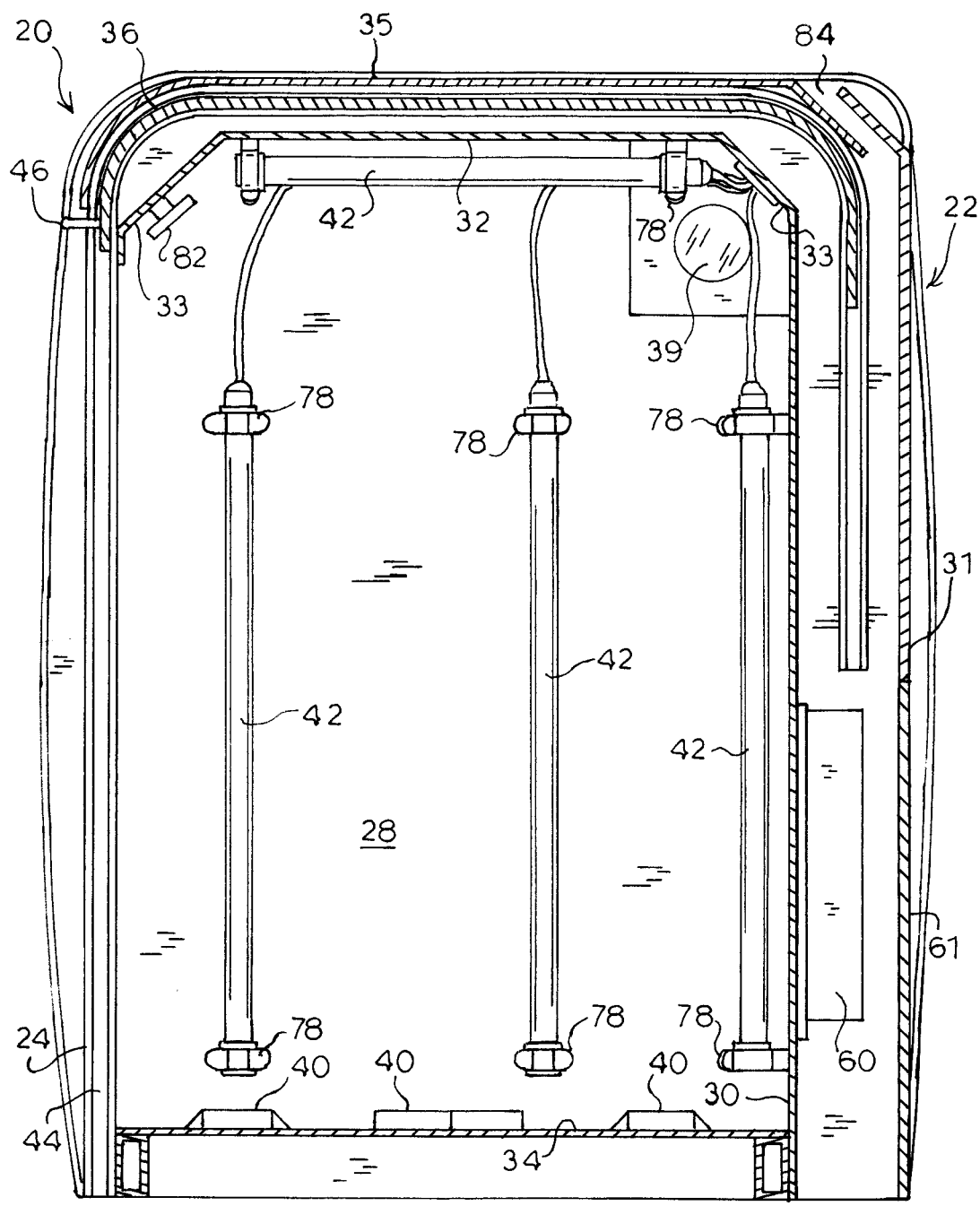
FIG. 3B is a longitudinal cross-section view of the sanitizing device shown in FIG. 3A with the mesh cages removed.

The door 36 is made of, or includes a layer, lining, or coating of, a material that is substantially opaque to UV radiation. The door 36 is slidingly received in a track 44 formed in the front wall 24 of the housing 22 (FIGS. 3A and 3B). The door 36 is slideable in the track 44 for moving between an open position (FIG. 2) wherein articles can be inserted into, or removed from, the chamber 38, and a closed position (FIG. 1) wherein the chamber 38 is closed so as to substantially prevent the escape of ultraviolet radiation from the chamber 38. A handle 46 of antimicrobial copper alloy may be provided on the door 36 for moving the door 36 between the open position and the closed position. A suitable light seal can be provided at a junction where the front wall 24 of the housing 22 and the leading edge of the door 36 engage when the door 36 is in the closed position. The seal may include any suitable material which inhibits the passage of light, such as a rubber or a felt gasket, or the door 36 may have a close or overlying fit between the door 36 and the front wall 24 of the housing 22.

Although the door 36 is shown as a tambour door, it is contemplated that the door 36 could alternatively be a hinged door or any other commercially suitable configuration. For example, the hinged door may be attached to the housing 22 by hinges disposed between the adjacent edges of the housing 22 and the door that allows the door to be selectively opened and closed.

The inner surfaces of the walls 24, 28, 30, the floor 34 and the ceiling 32 of the housing 22 are provided with a reflective material. A suitable material is aluminum, and more particularly, polished aluminum. Other metals may be used, such as polished zinc or stainless steel. Alternatively, a reflective coating may be placed on the inner surfaces of the walls 24, 28, 30, floor 34 and ceiling 32, such as magnesium carbonate. The reflective surfaces reflect the emitted UV radiation in order to ensure that all surfaces of the article to be irradiated receive comparable amounts of UV irradiation. In practice, a reflectivity in excess of 65% is desirable. In one embodiment, a polished aluminum can achieve up to 97% reflectivity, a polished zinc surface can achieve about 80% reflectivity, while the correct selection of magnesium carbonate/oxide coating can achieve about 70% reflectivity. The reflective inner surfaces of the walls 24, 28, 30, the floor 34 and the ceiling 32 of the housing 22 can be smooth, or if desired, may be a sculptured or otherwise non-planar configuration to enhance or direct the reflected radiation. In one embodiment, the inside surface of the door 36 may also be provided with a reflective material.

Figure 4:
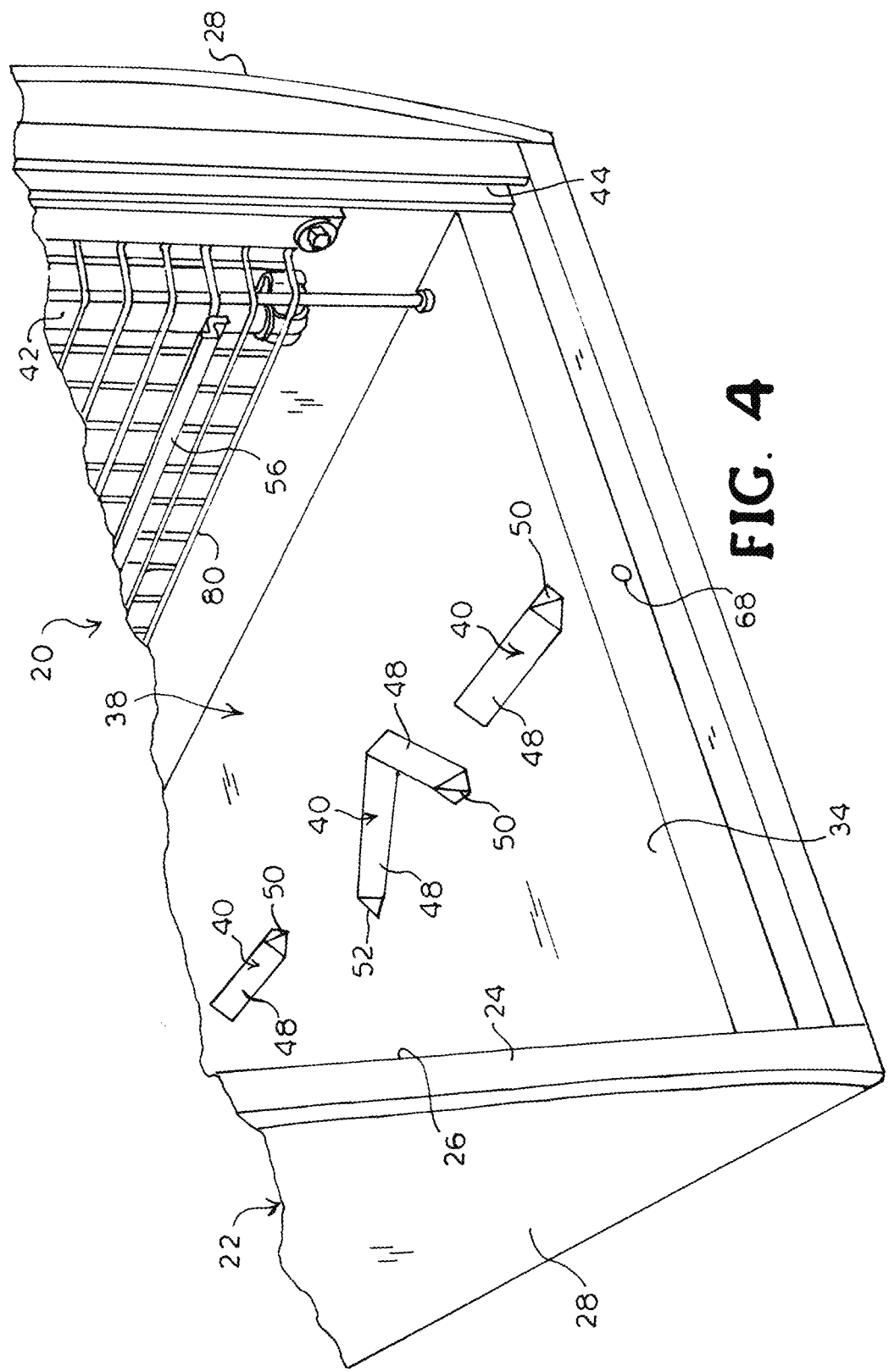
FIG. 4 is a close-up cut-away perspective view of an embodiment of reflector units on a bottom surface of the sanitizing device shown in FIG. 2.
Figure 5:
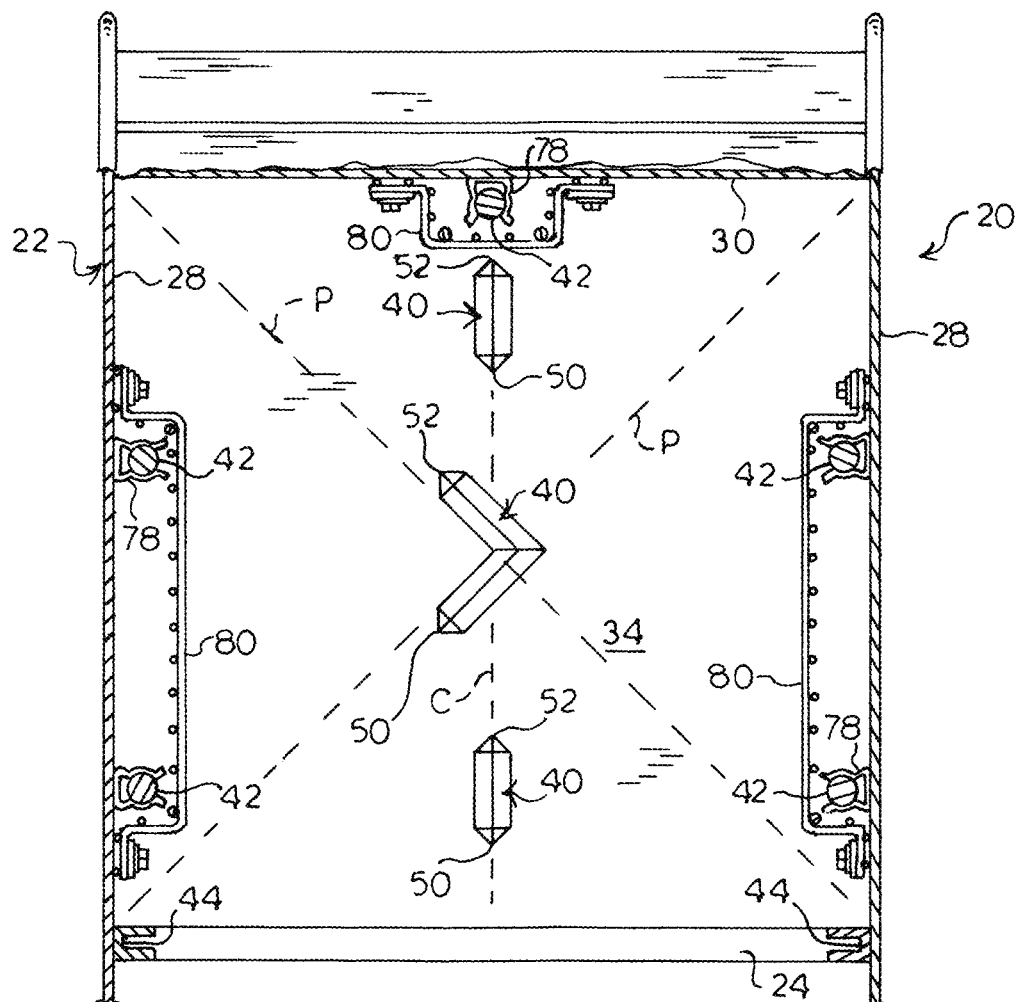
FIG. 5 is a cross-section view of the sanitizing device shown in FIG. 1 taken along line 5-5 of FIG. 2.
Figure 6:
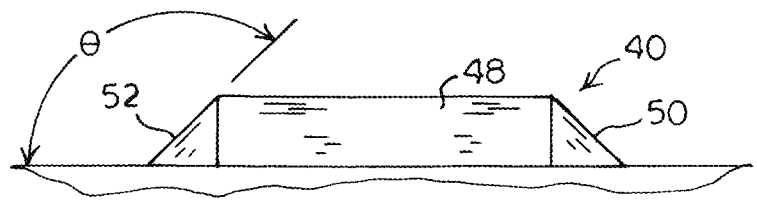
FIG. 6 is a side elevation view of an embodiment of a reflector unit for use in the sanitizing device shown in FIG. 1.

As shown in FIGS. 4 and 5, the floor 34 of the housing 22 includes a plurality of spaced reflector units 40. Referring to FIG. 6, each of a pair of sides of a reflector unit 40 includes at least three sections, a primary wall section 48, a first end wall section 50, and a second end wall section 52. The first and second end wall sections 50, 52 extend angularly inwardly from the primary wall section 48. Each of the three wall sections 48, 50, 52 extend upwardly from the floor 34 and are disposed off normal with respect to the floor 34. The angle (□) between the floor 34 of the housing 22 and each of the wall sections 48, 50, 52 is at least about 135 degrees. The wall sections 48, 50, 52 are joined at an apex of the reflector unit 40 forming an elongated pyramidal projection such that, when viewed from the front, the reflector unit 40 appears to have a triangular shape. In alternative embodiments, the reflector unit 40 could include four or more wall sections and be formed of shapes such that, when viewed from the front, the reflector unit 40 appears to have a square, rectangular, pentagonal, hexagonal, or any other commercially viable shape. Of course, depending on the shape of the reflector unit 40, the shape and number of reflective wall sections will likely vary.

The reflector units 40 can be composed of the same reflective material as the inner surfaces of the walls 24, 28, 30 of the housing 22. Alternatively, the reflector units 40 can be one or more commercially suitable materials, including, for example, mirrors, powder-coated and other metal sheets. The reflective wall sections 48, 50, 52 could also be dimpled or bumpy.

The reflector units 40 are positioned on the floor 34 with respect to the UV lamps 42 so that at least some UV radiation that would otherwise be emitted by the UV light sources in a direction other than at the articles is reflected upwardly toward the articles. Specifically, the longitudinal axis of each of the reflector units 40 adjacent the front and rear of the chamber 38 is aligned with the mid-line C (FIG. 5) between the side walls 28 of the chamber. The intermediate V-shaped reflector unit 40 is positioned such that a line P extending between each of the pairs of opposite corners of the housing 22 would be perpendicular to the primary wall sections 48 of the intermediate reflector unit 40.

With this arrangement of the reflector units 40, the UV radiation intensity on the various surfaces of the article is more consistent, which increases the efficiency of use of the UV radiation and maximizes the exposure of all surfaces of the articles to the UV radiation. The result is a sanitizing device 20 requiring fewer UV lamps 42 and a shorter duration of exposure to the UV light to disinfect the article. It is understood that the reflector units 40 can be disposed at any position on the inner surface of the walls 24, 28, 30, the ceiling 32 or the floor 34 of the housing 22 to achieve this result. All commercially suitable configurations for the reflector units 40 are contemplated, and such configurations will likely depend on the size and dimensions of the housing 22 and the articles to be irradiated.

Any commercially suitable source of UV radiation is contemplated for use with the sanitation device 20. The UV radiation source may include cold cathode UV tubes, LED's, and low, medium, or high vapor mercury lamps. The UV radiation source has a suitable wavelength that falls within the wavelength range of about 220 nm to about 300 nm, preferably at least substantially in the range of 235 nm to about 280 nm, and more preferably about 250 nm to about 275 nm. In this range, the UV radiation is highly effective against microorganisms.

Figure 7:
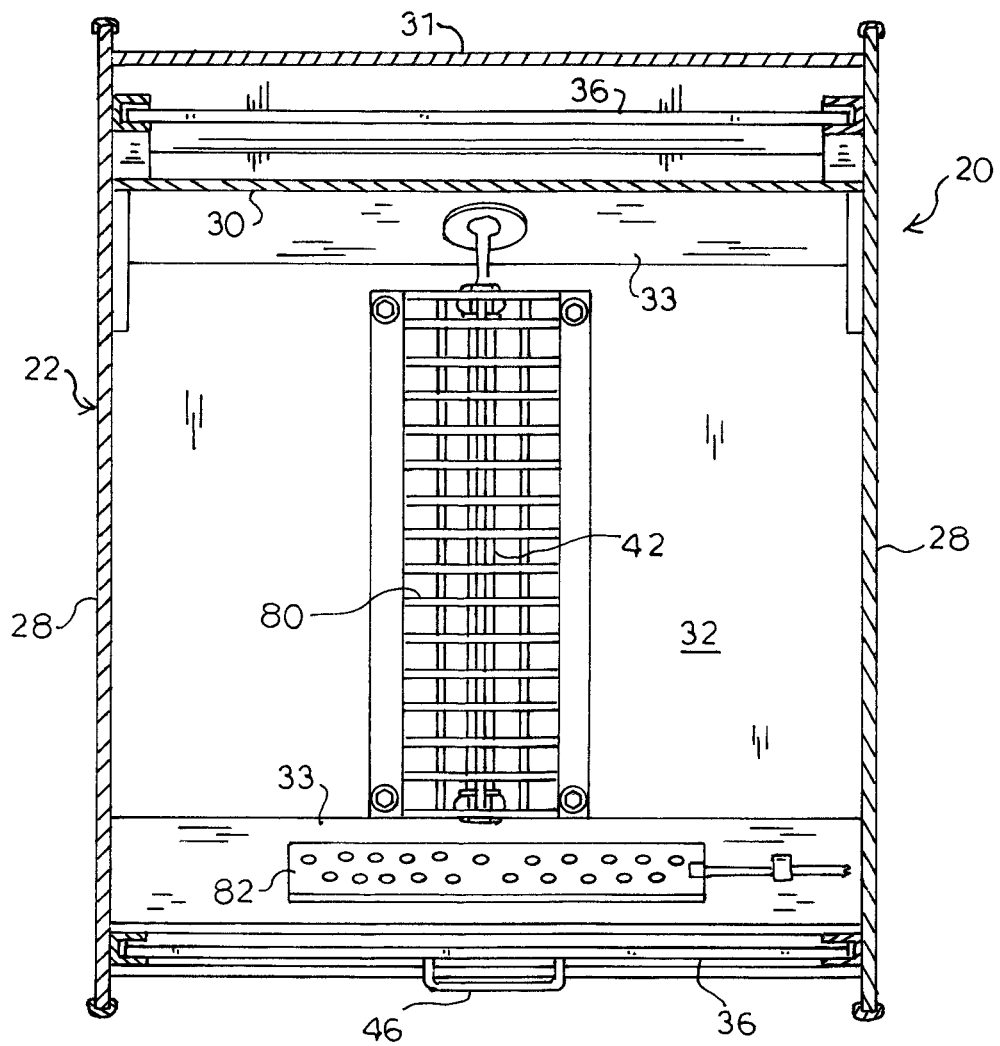
FIG. 7 is a cross-section view of the sanitizing device shown in FIG. 1 taken along line 7-7 of FIG. 2.

In the embodiment shown in FIGS. 2, 3B and 7, the source of UV radiation includes a plurality of elongated fluorescent UV lamps 42 disposed on an inner surface of the housing 22 and positioned to substantially irradiate the interior chamber 38 and any article in the chamber. A UV lamp that emits light within the preferred wavelength range and is suitable for use in the sanitizing device 20 is a Model No. GTL 18 or GTL 24 high output, 72 watt UV germicidal lamp, available from American Ultraviolet Company of Lebanon, Ind. These UV lamps are 15 mm glass tubes with a single end power connector and a protective boot and are Teflon-coated for containment in case of breakage. In addition, these UV lamps produce UV light at an intensity of 7200 $\mu W/cm^2$ at a distance of about twelve inches. The UV lamps are approximately 18 inches and 24 inches in length, respectively, including three inches attributed to the end connectors. Although the UV lamps are shown having elongated tubular bulbs, it is contemplated that other commercially suitable sources of UV light could be used of any convenient size or shape of UV lamp or bulb may be employed. Even a plurality, or a bank, of UV LED's may be employed, as long as they emit the proper wavelength of UV light.

The plurality of UV lamps 42 are attached to pairs of tube holders 78 and depend from the inside surface of each of the side walls 28, the inner rear wall 30 and the ceiling 32 of the housing 22. The UV lamps 42 are oriented radially inward towards the center of the chamber 38 so as to provide UV radiation from all directions to maximize the exposure of the articles within the chamber 38. The UV lamps are spaced about 1½ inches from the inner surfaces of the housing 22. Two UV lamps 42 are provided on each side wall 28 extending generally vertically and are evenly spaced between the floor 34 and the ceiling 32. The front UV lamp 42 on each side wall 28 is spaced about 4 inches from the front wall 24, and the rear UV lamp 42 on each side wall 28 is spaced about 8 inches from the rear wall 30. The front and rear UV lamps 42 are spaced from each other about 10 inches on center. The single UV lamp 42 on the rear wall 30 is disposed along the central longitudinal axis of the rear wall 30 and is evenly spaced between the ceiling 30 and the floor 34. The UV lamp 42 on the ceiling 32 is disposed along the central longitudinal axis of the ceiling 32 and is evenly spaced between the front wall 24 and the rear wall 30. The distance from each of the UV lamps to a central plane passing through the middle of the chamber 38 is about eleven inches. In one embodiment of the sanitizing device 20 based on these relative dimensions, the reflector units 40 may each be about 4 inches in length and project upwardly about ¾ inches from the floor 34 of the housing 22. The front end of the front reflector unit 40 is about 1½ inches from the front wall of the housing 22 and the rear end of the rear reflector unit 40 is about three inches from the rear wall 30. For the V-shaped reflector unit 40, the length of four inches is measured from the point of the "V" to each end.

It is understood that the UV lamps 42 could be disposed at non-right angles. It is further understood that the specific number, size, and orientations of each of the UV lamps 42 will likely vary depending on the size and type of UV lamps used, the article to be disinfected, and the sizes and dimensions of the housing 22. The UV lamps 42 can be disposed in any suitable locations and oriented such that articles within the chamber 38 are exposed to adequate amounts of UV radiation for sanitization. A wire mesh protective cage 80 surrounds each of the UV lamps 42.

Figure 8:
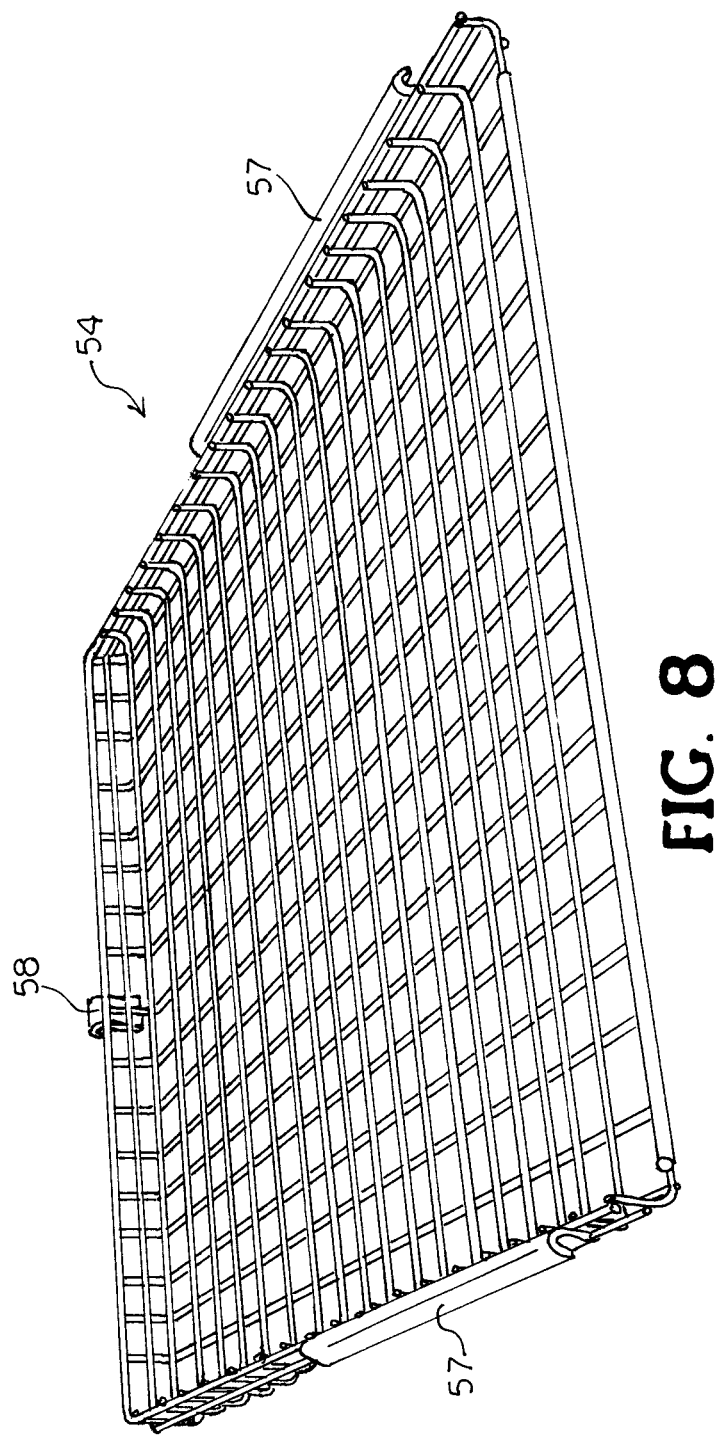
FIG. 8 is a perspective of an embodiment of a tray for use in the sanitizing device shown in FIG. 1.

The article supporting means may comprise an article support suitable for use in the environment of the chamber 38, such as a drawer, tray, shelf system, or receptacles for receiving and supporting articles within the housing 22. In the embodiment shown in the FIGS., the article supporting means is a plurality of trays 54 positioned at different levels in the chamber 38. Referring to FIG. 8, each tray 54 comprises a platform disposed in a flat configuration. The tray 54 is formed from a light-transmissible material made of wire mesh or lattice such as, for example, 50 mm wire mesh. The tray 54 is configured to have some depth thereby defining a recess for accommodating the article. Opposed channels 56 are provided on the inner surfaces of the side walls 28. Elongated downwardly curved flanges 57 are positioned on opposite sides of the trays 54 for slidably receiving the channels 56. A hook 58 is provided on the back edge of the tray 54. The hook 58 captures the wire mesh of the cage 80 surrounding the UV lamp 42 on the rear wall 30 to secure the trays 54 in an inserted position. The trays 54 can be removed for cleaning or for loading articles on the trays 54.

The relative positioning of the UV lamps 42, the reflector units 40, and the trays 54 is such as to ensure that all surfaces of the article and the upper and lower surfaces of the trays 54 are exposed to sufficient amounts of UV irradiation through the apertures of the wire mesh. The effect of "shadows" caused by the bars of the mesh coming between the lower surface of the article when supported on the mesh and the UV radiation are minimized. The channels 56 and flanges 57 are made of reflective material to further maximize the distribution of UV radiation. A minimal contact area between the article and the mesh of the tray 54 may be acceptable.

Figure 9:
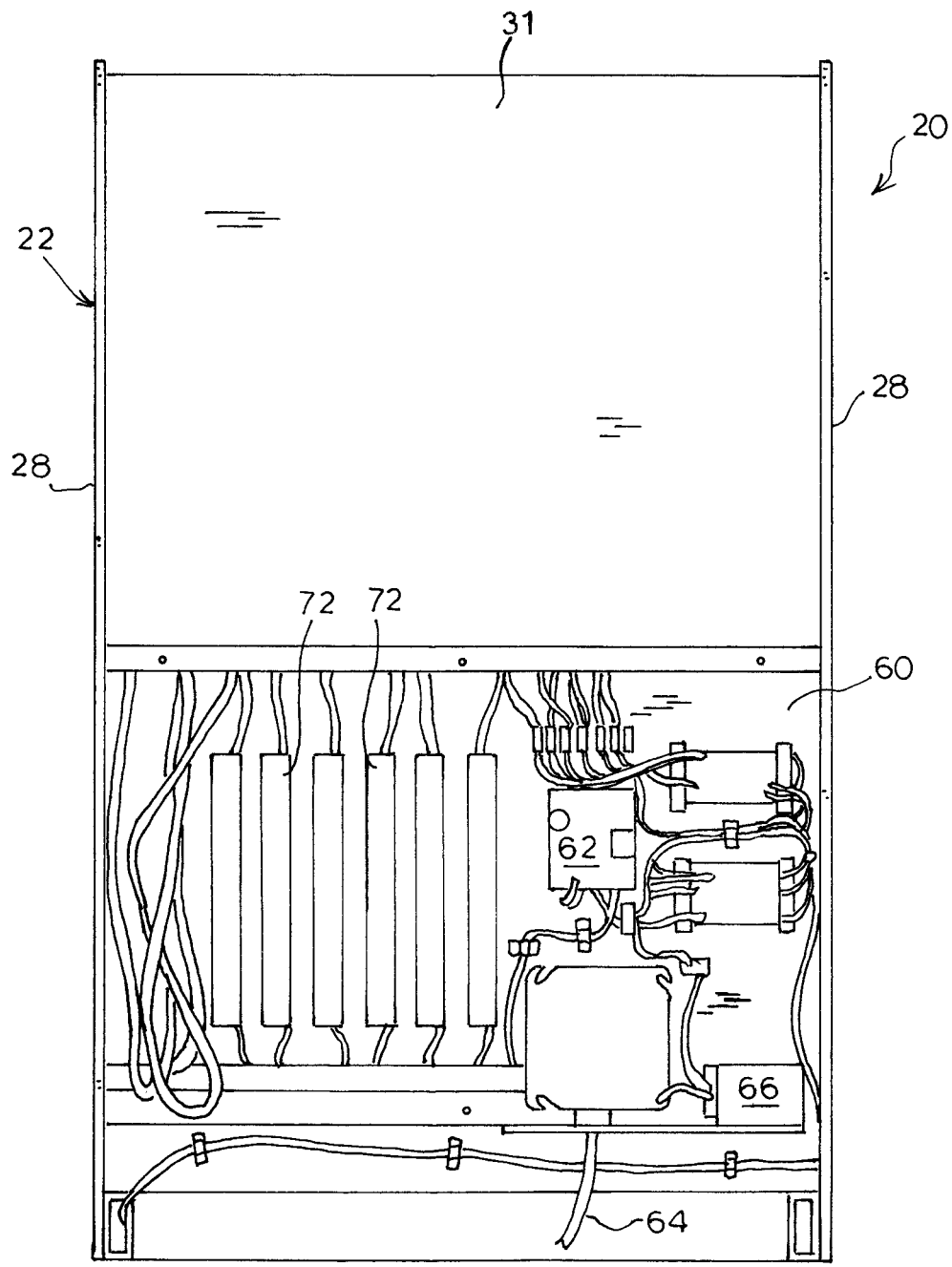
FIG. 9 is a rear elevation view of the sanitizing device shown in FIG. 1 with a partial cover panel removed.
Figure 10:
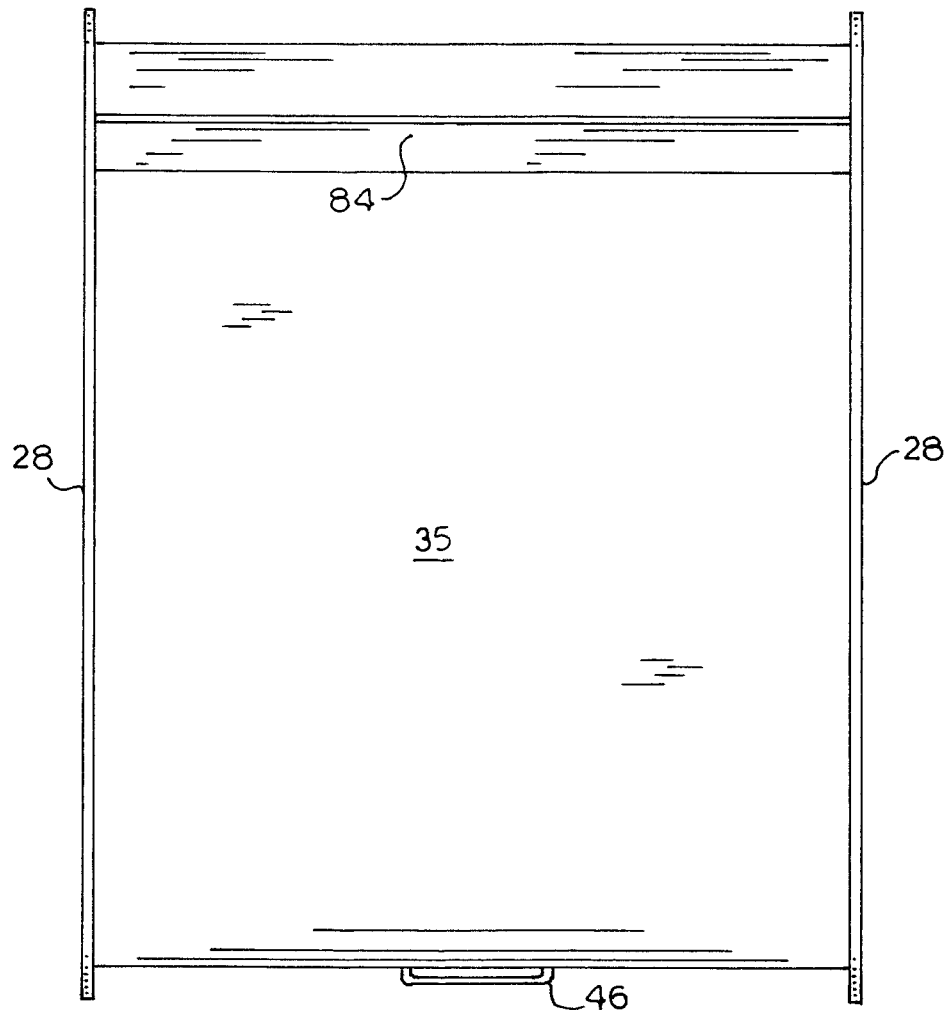
FIG. 10 is a top plan view of the sanitizing device shown in FIG. 1.

Referring now to FIG. 9, the outer surface of the rear wall 30 of the sanitizing device 20 accommodates a control box 60. The control box 60 preferably has a removable cover panel (not shown) for allowing access to a circuit board supporting the wiring and circuitry for repair, removal, and replacement. The circuit board carries a controller 62 for controlling operation of the sanitizing device 20 and a power supply 64 for providing power to the controller 62, such as electric cord and plug (not shown). The power supply cord 64 is connected to a transformer 66 to provide electrical power to the circuit. The controller 62 can control the delivery of power to the UV lamps 42 to be turned on or off, as well regulating other electrical components of the sanitizing device 20 including, for example, one or more sensors.

A first sensor 68 senses or detects whether the door 36 is in the open position or the closed position and signals the controller to control operation of the sanitizing device 20 accordingly. Alternatively, a sensor may be activated upon closing the door. The sensor can include, but is not limited to, one or more of a depression switch, electrical contacts, an optical sensor or other sensor known in the art for determining the relative positions of the door and the front wall 24 of the housing 22. In one embodiment, the sensor comprises a contact on the housing 22 and a magnet 69 in the door 36, the completed circuit activating the UV radiation source only when the door 36 is in the closed position to enclose the chamber 38. For example, the ultraviolet radiation source is disabled from emitting ultraviolet light when the door 36 is in the open position and is enabled to emit ultraviolet light when the door 36 is in the closed position.

Each UV light source is electrically connected to an electronic ballast, which provides resistance to stabilize current in the circuit created when the sanitizing device 20 is attached to a power source via the power supply cord 64. In a preferred embodiment, ballast is operational with 100/200 VAC at 50/60 HZ.

In one embodiment, the controller 62 activates the ultraviolet radiation source for a first predetermined period of time when the sensor 68 senses that the door 36 is in the closed position. The predetermined period of time may vary depending on the strength of the UV light source. In one embodiment of the sanitizing device 20 using the 72 watt UV lamps identified above, it is estimated that between about 30 and about 60 seconds would be sufficient to eliminate most bacteria present on an article. A timer is used to control the length of time the UV source is powered. The controller 62 automatically turns off the UV light source at the set time on the timer after, for example, the about 30 to about 60 seconds, and may include an audible signal (beep, chime, etc.) to let the user know the cycle is finished. The controller may in addition to, or alternately, activate the UV radiation source based on a signal from a manual interface, such as a switch 70 (FIG. 1) or other interface located outside of the sanitizing device 20 that a user can select to manually activate the controller 62. A plurality of switches may also be provided, and additional functionality may be included, including different settings for different articles to be sanitized, different durations of the sanitization cycle, different power level intensities for the UV lamps, and the like.

One or more indicator lamps or displays may be provided on the outside of the housing 22 to indicate the status of the sanitizing device 20. For example, a lamp indicator light may show whether power is being sent to the sanitizing device 20. A light 82 may also be provided in the chamber 38 (FIG. 7), which light 82 is activated for the user when the door 36 is in the open position. All other commercially viable safety systems are contemplated. For example, a vent 84 is provided between the rear walls 30, 31 of the housing 22 and exits via the roof 35. The sanitizing device 20 could also require a key or security code be entered prior to activation.

In operation, the user moves the door 36 to the open position by rolling upwardly to expose the chamber 38 and the trays 54. The trays 54 are accessed by manually detaching the hooks 58 and pulling the trays 54 outwardly. The trays 54 slide along the channels 56 and may be completely removed. Articles to be irradiated are then placed on one or more of the trays 54. The trays 54 are then returned to the chamber 38 and pushed inwardly to the closed position by pressing on the front of the trays 54 and attaching the hooks 58 to the wire mesh of the cage 80. The user moves the door 36 to the closed position to enclose the articles within the chamber 38. The sensor 68 is activated upon closing of the door 36 for signaling the controller 62 that the door is in the closed position. The sanitizing device 20 is activated by pressing the outside switch 70. Upon activation, the controller 62 directs power to energize the UV lamps 42 to sanitize the articles.

When the sanitization device 20 is activated, UV light is directed throughout the chamber 38 and onto the articles to be disinfected. UV light is reflected off of the reflective inner surfaces of the walls and the surfaces of the reflector units 40 ensuring exposure of all surfaces of the articles to UV light. The effect is UV light is directed from the UV lamps 42 in all directions, including irradiating the underside of the articles through the apertures in the trays 54. The UV light kills significant amounts of microorganisms that may be on the articles, thereby sanitizing, or disinfecting, the articles. The articles are subjected to a dose of UV light corresponding to the UV light intensity as a function of time and distance of the UV lamps from the articles. Dose response levels are unique to each microorganism. Additionally, different wavelengths of UV light have different inactivation rates depending on the microorganism. It is understood that such process parameters are predetermined to affect the amount of radiation such that an article receives UV light sufficient to destroy microorganisms on the surfaces of the articles and to ensure a consistently effective reduction in microbial numbers.

After a predetermined time sufficient to achieve a desired level of sanitization, the controller 62 deactivates the UV radiation sources. When the sanitization cycle is completed, the display may indicate as such. If the sensor 68 detects an attempt to open the door 36 while the UV radiation sources are activated, the controller immediately shuts off power to the UV radiation sources.

It is contemplated that the sanitizing device 20 described and shown herein could be configured to sanitize all manner of articles and equipment including, for example, cosmetics or cosmetic implements such as eyeliner brushes and mascara brushes, and even small cosmetic items themselves such as personal items including compacts, and the like; kitchen utensils and tools such as cutting boards, and larger sized items including wheel chairs, strollers, and other sizes of shopping carts shopping baskets. Depending on the size and dimension of sanitizing device 20, and the type of equipment to be disinfected, the number of reflective units, and their configurations, can be varied. Regardless of the article to be sanitized, the sanitizing device 20 design allows for considerable adjustment of the amount of energy striking the article by selecting the number of lamps used, the distance of those lamps from the article, and the length of time that the article is exposed to UV light. The sanitizing device 20 can conveniently and effectively disinfect articles in a short period of time.

The sanitizing device 20 described and shown herein was tested to determine the efficiency of the sanitizing device 20 versus a concentration of *Clostridium difficile* (*C. difficile*), *Staphylococcus aureus* (*S. aureus*), and *Acinetobacter baumannii* (*A. baumannii*) using a 60 second exposure time and a 120 second exposure time. Microorganism preparation included inoculating tryptic soy agar (TSA) petri plates with *S. aureus* and *A. baumannii* and incubating the plates for 22-26 hours at 30-35° C. Similarly, reinforced clostridial medium plus agar (RCM+Agar) petri plates were inoculated with *C. difficile* and incubated for 46-52 hours at 30-35° C. in an anaerobic chamber containing an AnaeroGen Pak™.

Serial dilutions of each culture were prepared in 7.2 pH buffer. Next, 0.1 mL of $10^3$ CFU/mL concentration of each organism were plated in duplicate and incubated as described above. The concentration of each organism was calculated by multiplying the count acquired by 10 due to the $10^4$ CFU/mL dilution being used for spiking.

Pre-poured plates were then spiked. Specifically, 18 TSA plates were inoculated with 0.1 mL of $10^4$ CFU/mL of *S. aureus* and spread with a sterile hockey stick and another 18

TSA plates were inoculated with 0.1 mL of $10^4$ CFU/mL of *A. baumannii* and spread with a sterile hockey stick. Similarly, 18 RCM+Agar plates were inoculated with 0.1 mL of $10^4$ CFU/mL of *C. difficile* and spread with a sterile hockey stick.

The organism-spiked plates were then placed in the sanitizing device 20 on each of the top, middle and bottom trays. On the top tray, plates were placed at the right front, back middle and left back of the tray. On the middle tray, plates were placed at the right back, middle and left middle of the tray. On the bottom tray, plates were placed at the right middle, middle, and left front of the tray. Lids were removed from the plates and the plates set agar side up. The sanitizing device 20 was activated for 60 seconds. The sanitizing device was deactivated and the lids replaced on the plates and the plates removed. These steps were repeated for each organism.

In a second run, the organism-spiked plates were in the sanitizing device 20 on each of the top, middle and bottom trays. On the top tray, plates were placed at the middle front, left back and right back of the tray. On the middle tray, plates were placed at the middle back, middle and left front of the tray. On the bottom tray, plates were placed at the right front, middle front, and left back of the tray. Lids were removed from the plates and the plates set agar side up. The sanitizing device 20 was activated for 120 seconds. The sanitizing device was deactivated and lids replaced on the plates and the plates removed. These steps were repeated for each organism.

The UV treated plates of *S. aureus* and *A. baumannii* were incubated at 30-25° C. for 44-52 hours. The UV treated plates of *C. difficile* were incubated at 30-35° C. for 44-52 hours in an anaerobic jar containing an AnaeroGen Pak™. The organism spike count from untreated plates served as a positive control to confirm that TSA and RCM+Agar media supported the correct bacterial growth. An un-spiked TSA plate and an un-spiked RCM+Agar plate were also incubated to confirm that the plates were not contaminated.

The percent kill of each organism for each exposure time was calculated by dividing the count after the exposure to UV light by the original concentration of the organism and then multiplying by 100. $Log_{10}$ reduction of each organism for each exposure time was calculated by converting each organism count to a $log_{10}$ number. For example, 213 CFU/mL equals 2.33 $Log_{10}$. The $Log_{10}$ decrease of each organism for each exposure time was found by calculating the difference between the $Log_{10}$ of the original concentration of the organism and the $Log_{10}$ after the 60 and 120 second exposure to UV.

The sanitizing device 20 for all plates at all locations and for both exposure times achieved a 100% killing of *S. aureus* and *A. baumannii*. The sanitizing device 20 for all plates at all locations and for both exposure times achieved a 100% killing of *C. difficile*, except for the middle tray at the middle and left middle locations, which achieved 99.9% reduction in the organism. Converting the organism counts to a $Log_{10}$ number, the reduction in *S. aureus* at all locations was 5.80 $log_{10}$ and the reduction in *A. baumannii* at all locations was 6.15 $log_{10}$. Although one colony of was found on two of the *C. difficile* plates from the 120 second exposure study, the $log_{10}$ of 1 is 0 so the $log_{10}$ reduction for all locations was 4.00.

Although the apparatus and method for sanitizing articles has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. Accordingly, we intend to cover all such modifications, omission, additions and equivalents as may be included within the spirit and scope of the invention as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

I claim:

1. An apparatus for sanitizing an article, the apparatus comprising:
   a housing including a plurality of walls, a ceiling, and a floor, the plurality of walls, the ceiling and the floor interconnected for defining an enclosed internal chamber, one of the plurality of walls having an opening at a door side into the chamber;
   a door configured to selectively close the door side of the housing for substantially sealing the chamber;
   a UV light source disposed on at least one of the plurality of walls internally of the housing for irradiating the chamber;
   an electronic circuit electrically connected to the UV light source and adapted to power the UV light source for a predetermined period of time; and
   a plurality of reflector units disposed on floor of the housing, each reflector unit including a reflective section comprising
      a pair of major planar side surfaces, the side surfaces projecting into the chamber at an angle other than normal with respect to the floor of the housing, the side surfaces joining at a common longitudinal edge along a central longitudinal axis of the reflector unit,
   the plurality of reflector units comprising
      a pair of spaced linear reflector units positioned such that the central longitudinal axis of the pair of reflector units extends along a midline of the floor between two of the plurality of walls defining the chamber, and
      a central reflector unit disposed between the pair of linear reflector units on the midline, the major planar side surfaces of the central reflector unit comprising
         a first portion, and
         a second portion angled with respect to the first portion, each of the first portion and the second portion of the major side surfaces having a central longitudinal axis that is perpendicular to at least one axis extending between the corners of the walls,
   wherein with the article placed in the chamber and the door closed and the electronic circuit activated the UV lamp is powered for the predetermined period of time such that UV light from the light source and UV light reflected back into the chamber by the plurality of reflector units illuminates the article for sanitizing the article.

2. The apparatus for sanitizing an article as recited in claim 1, further comprising a tray configured to be received in the chamber of the housing, wherein the tray is adapted for supporting the article.

3. The apparatus for sanitizing an article as recited in claim 2, wherein the tray comprises a wire mesh.

4. The apparatus for sanitizing an article as recited in claim 1, wherein the UV light source provides an intensity of about 7200 µW/cm² of UV light at about one foot.

5. The apparatus for sanitizing an article as recited in claim 1, wherein the reflective section of the reflector unit is angled with respect to the floor by at least about 135 degrees.

6. The apparatus for sanitizing an article as recited in claim 1, wherein the plurality of the walls of the housing comprises a front wall and an opposite rear wall, a pair of side walls interconnecting the front wall and the rear wall, the floor interconnecting the lower edges of the front wall, the rear wall and the side walls, and the ceiling interconnecting the upper edges of the front wall, the rear wall and the side walls.

7. The apparatus for sanitizing an article as recited in claim 6, wherein the UV light source extends along the rear wall.

8. The apparatus for sanitizing an article as recited in claim 6, further comprising a plurality of UV light sources extending along the plurality of the walls of the housing.

9. The apparatus for sanitizing an article as recited in claim 1, wherein a cross-section of each of the plurality of reflector units taken along the central longitudinal axis is a triangle.

10. The apparatus for sanitizing an article as recited in claim 1, further comprising end wall surfaces projecting into the chamber from the floor of the housing, each of the end walls surfaces extending inwardly from a respective longitudinally spaced terminal edge of the major side surfaces and joining at a common edge for forming terminal ends of each of the plurality of reflector units.

11. The apparatus for sanitizing an article as recited in claim 10, wherein each of the plurality of reflector units is a substantially elongated pyramid projecting into the chamber.

12. The apparatus for sanitizing an article as recited in claim 1, wherein the side surfaces of each of the plurality of reflector units comprise a metal.

13. The apparatus for sanitizing an article as recited in claim 12, wherein the metal is selected from aluminum, zinc, magnesium carbonate/oxide or combinations thereof.

14. The apparatus for sanitizing an article as recited in claim 12, wherein the metal is a powder-coated metal on the side surfaces of the reflector unit.

15. The apparatus for sanitizing an article as recited in claim 1, wherein the side surfaces of each of the plurality of reflector units comprise mirrors.

* * * * *